United States Patent [19]
Picha et al.

[11] Patent Number: 5,356,382
[45] Date of Patent: Oct. 18, 1994

[54] PERCUTANEOUS TRACT MEASURING AND FORMING DEVICE

[75] Inventors: George J. Picha, Independence; Angela P. Nguyen, Sagamore Hills; Jim Gelbke, Strongsville, all of Ohio

[73] Assignee: Applied Medical Research, Inc., Independence, Ohio

[21] Appl. No.: 965,219

[22] Filed: Oct. 23, 1992

[51] Int. Cl.5 .......................................... A61M 25/00
[52] U.S. Cl. ................... 604/105; 606/185; 606/198; 128/780
[58] Field of Search ............... 604/104–109, 604/117, 164; 128/774, 780; 606/191, 198, 184, 185

[56] References Cited

U.S. PATENT DOCUMENTS

| | | |
|---|---|---|
| 2,649,092 | 8/1953 | Wallace . |
| 3,241,554 | 3/1966 | Coanda . |
| 3,934,721 | 1/1976 | Juster et al. . |
| 3,946,741 | 3/1976 | Adair ............................ 604/105 |
| 4,062,363 | 12/1977 | Bonner, Jr. . |
| 4,393,873 | 7/1983 | Nawash et al. . |
| 4,500,313 | 2/1985 | Young . |
| 4,551,137 | 11/1985 | Osborne . |
| 4,608,965 | 9/1986 | Anspach ......................... 604/105 |
| 4,612,939 | 9/1986 | Robertson . |
| 4,758,219 | 7/1988 | Sacks et al. . |
| 4,762,519 | 8/1988 | Frimberger . |
| 4,781,682 | 11/1988 | Patel ............................. 604/104 |
| 4,808,163 | 2/1989 | Laub ............................. 606/198 |
| 4,850,953 | 7/1989 | Haber et al. . |
| 4,863,438 | 9/1989 | Gauderer et al. . |
| 4,944,732 | 7/1990 | Russo . |
| 4,972,845 | 11/1990 | Iversen et al. . |
| 4,981,470 | 1/1991 | Bombeck, IV . |
| 4,986,810 | 1/1991 | Semrad . |
| 5,041,093 | 8/1991 | Chu ............................... 604/104 |
| 5,074,846 | 12/1991 | Clegg et al. . |
| 5,074,871 | 12/1991 | Groshong ...................... 606/198 |
| 5,084,014 | 1/1992 | Picha et al. . |
| 5,122,122 | 6/1992 | Allgood ......................... 604/105 |

OTHER PUBLICATIONS

U.S. Patent Application Serial No. 07/767,124, filed Sep. 27, 1991, entitled "Tract Measuring Device".
Gauderer et al. "The Gastrostomy 'Button'"—A Simple, Skin-Level, Nonrefluxing Device for Long-Term Enternal Feedings, Journal of Pediatric Surgery, vol. 16, No. 6, Dec. 1984—pp. 803–805.
Ponsky et al. "Percutaneous endoscopic gastrostomy: a non-operative technique for feeding gastrostomy," Gastrointestinal Endoscopy, vol. 27, No. 1, 1981, pp. 9–11.

*Primary Examiner*—John D. Yasko
*Assistant Examiner*—Anthony Gutowski
*Attorney, Agent, or Firm*—Pearne, Gordon McCoy & Granger

[57] ABSTRACT

A surgical tool for use in initial placement of a gastrostomy device in a patient includes an obturator, a cannula and an outer flexible tubular member. A pointed end of the obturator and an adjacent dilator cooperate to incise a tract through the abdominal and stomach walls of the patient. The obturator is removed, leaving the cannula and outer tubular member in place. A deformable section of the flexible tubular member is expanded by movement of the cannula. The outwardly deformed section is then pulled up against the inner wall of the stomach wherein the thickness of the stomach and abdominal walls can be measured by use of visible scale indicia carried on the external surface of the flexible tubular member. Subsequent to the noted measurement, a guidewire or pull wire is passed through a lumen provided by the cannula. The guidewire is used for placing a gastrostomy device of suitable size in the incised tract.

20 Claims, 4 Drawing Sheets

PERCUTANEOUS TRACT MEASURING AND FORMING DEVICE

BACKGROUND OF THE INVENTION

1. Field of the Invention

The present invention relates in general to tract measuring devices and, in particular, to a surgical tool adapted to create and to measure the length of an incised tract.

2. Description of the Related Art

Over the years, devices have developed to allow fluid communication between an interior body cavity and an external surface of the body. Specifically, enteral feeding tubes and gastrostomy devices have been developed to provide nourishment to patients unable to otherwise ingest food due to the effects of a stroke, coma, serious injury or other medical problem.

Enteral feeding tubes are generally used only for limited periods of time while gastrostomy devices and, preferably low-profile gastrostomy devices, are used in long-term or permanent installations. A primary consideration during installation of either the feeding tube or the gastrostomy device is the relatively precise installed fit necessary to prevent infection, the migration of bodily fluids from the internal body cavity, and the proper formation of a mature stoma.

Since the length of the tract from the external surface to the inner body cavity varies from patient to patient due to various factors such as age, weight, and sex, the enteral feeding tube, which is typically adjustable to accommodate a range of incised tract lengths, is conventionally initially installed within the incised tract regardless of the anticipated period of need for fluid communication between the inner body cavity and the external surface. Thereafter, if long-term fluid communication is required, the feeding tube is removed and replaced by a gastrostomy device. The gastrostomy device is typically not adjustable to accommodate multiple tract lengths and therefore must be custom-fit to closely match the incised tract length for each patient.

Preliminary to the installation of any device to extend between the external surface of the body and the interior body cavity, an incised tract must be formed. The incised tract is conventionally formed by inserting a trocar and cannula through the external body surface and into the internal body cavity. Thereafter, the enteral feeding tube is installed within the just-formed tract.

Such an enteral feeding tube, as represented by U.S. Pat. No. 4,758,219, is typically introduced into the stomach via the mouth and esophagus, and then partially removed from the incised tract formed by a previously-inserted trocar and cannula. An internal end of the feeding tube mountingly accommodates an enlarged portion serving as a stop means while an external end of the feeding tube includes an adjustable skin protecting ring or bolster. The distance between the stop means and the bolster is adjusted by moving the bolster along the length of the feeding tube, firmly trapping the external surface of the body and the inner wall of the internal body cavity between the ring and stop means.

Other enteral feeding tubes are designed to be inserted through the incised tract from the external body surface into the internal body cavity, and include an internal end portion which is inflatable or otherwise expandable to define a stop surface. U.S. Pat. No. 5,074,846 is exemplary of devices of this type. A lengthwise adjustable outer skin engaging ring or bolster is used to compensate for variations in tract length, as in the '219 patent.

Outwardly deformable tubes or sheaths similar to the type shown in the '846 patent have also been used in catheters to retain the inner end of the catheter within an inner body cavity such as the bladder or peritoneum, as evidenced by U.S. Pat. Nos. 2,649,092 and 3,241,554. The catheter of the '554 patent also includes a depth gauge to indicate how far the catheter has been inserted into the abdominal wall.

Although the devices and methods for installing enteral feeding tubes illustrated above are satisfactory for short-term use, such feeding tubes are generally considered undesirable for long-term or permanent use due to the external length of the tube and awkwardness associated therewith. Therefore, for long-term installations, a low-profile gastrostomy device preferably replaces the enteral feeding tube after a mature stoma between the exterior body surface and internal body cavity has been established. The gastrostomy device, which, due to its low-profile nature, does not include a length adjustment feature, must be specifically sized to match the stoma length.

Therefore, prior to installation of a gastrostomy device, the stoma length is conventionally determined by measuring the length of the feeding tube from the external surface of the body to the internal stop surface. Typically, this is accomplished by placing a reference mark on the feeding tube adjacent the external surface, removing the feeding tube from the body by reversing the installation steps, and then measuring the distance from the reference mark to the stop surface. The appropriate size of the gastrostomy device is derived from this measurement. Thereafter, the gastrostomy device is inserted into the stoma to complete the replacement procedure.

Alternatively, stoma length can be determined by a measuring device such as disclosed by U.S. Pat. No. 4,972,845. The stoma measuring device of the '845 patent includes an elongated tubular member which provides scale indicia on an exterior surface thereof. A distal end of the tubular member is inflatable to serve as a stop means to temporarily prevent the removal of the distal end from an inner body cavity, allowing the length of the stoma to be measured via the scale indicia.

U.S. Pat. No. 4,863,438, which is assigned to the assignee of the present invention and expressly incorporated herein by reference, is exemplary of low profile gastrostomy device which is designed to replace an enteral feeding tube within an existing stoma. A stylet is used to elongate and stretch the enlarged intragastric head of the gastrostomy device, which is thereafter pushed through the stoma into the internal body cavity. A tubular midportion is received by the stoma while a pair of oppositely directed wings engage the external body surface. Additional gastrostomy feeding ports are shown in U.S. Pat. Nos. 4,850,953 and 4,944,732.

In all of the aforementioned gastrostomy devices, the gastrostomy device must fit snugly within the stoma between the inner wall of the internal body cavity and the external body surface. In the aforementioned prior art this has necessitated the initial installation of an enteral feeding tube in the incised tract to allow the incised tract to mature and become a permanent stoma and to thereafter allow an accurate measurement of the stoma length.

Therefore, in the aforementioned prior art, the steps of forming an incised tract, inserting an enteral feeding tube, allowing the incised tract to mature into a stoma, removing the enteral feeding tube, and measuring the stoma length are required before the gastrostomy device can be installed within the stoma.

In response to this costly and time consuming process, it has been proposed that a low-profile gastrostomy device be directly installed within an incised tract without the need for the preliminary placement of a feeding tube therein. Initially placing a low-profile gastrostomy device in an incised tract allows the patient to immediately benefit from the advantages inherent in use of a low profile gastrostomy device as opposed to an enteral feeding tube. Moreover, eliminating the need for the initial placement of a feeding tube reduces the cost and trauma traditionally associated with the installation of a gastrostomy device. U.S. Pat. No. 5,084,014, which is owned by the assignee of the present invention and expressly incorporated herein by reference, is directed towards a low-profile gastrostomy device adapted to be mounted within a recently-formed incised tract.

The '014 patent discloses a package for the initial placement of a gastrostomy device wherein an external body surface-engaging portion is outwardly pulled through the incised tract. The package includes a shroud which retains wing-like members of the external body surface-engaging portion in a deformed configuration, generally parallel to a tubular midportion of the device. Installation occurs by inserting the package into the stomach, pulling it through the incised tract until an enlarged intragastric portion engages the inner wall of the stomach, and thereafter removing the shroud to allow the wings to return to their undeformed, outwardly extending configuration. Once installed, the device functions generally identically to the gastrostomy device disclosed in the '438 patent.

Although the installation package of the '014 patent works satisfactorily, proper sizing of the gastrostomy device still requires the prior measurement of the incised tract length.

United States patent application Ser. No. 07/767,124, which was filed on Sep. 27, 1991, entitled "TRACT MEASURING DEVICE", the disclosure of which is expressly incorporated herein by reference, is directed towards a device and method for measuring the length of an incised tract. The device includes an elongated member having scale indicia along at least a portion of its length, and stop means at one end of the scale indicia.

In the disclosed method of the '124 application, an incised tract between an external surface of a body and an inner wall of an internal body cavity is formed by a trocar and cannula. Thereafter, the device is inserted into the stomach via the mouth and esophagus, and a distal end of the elongated member is inserted through the incised tract until the stop means engages the inner wall of the internal body cavity. The elongated member extends out of the incised tract, making the scale indicia thereon visible and allowing the determination of tract length. Thereafter, the incised tract measuring device is removed and a low profile device sized to match the measured tract length is installed, preferably in accordance with the device and method of U.S. Pat. No. 5,084,014.

Although the aforementioned incised tract measuring device and method represents an improvement over the prior art method of measuring length, it suffers from the disadvantage that it requires insertion and removal via the esophagus, creating additional irritation and trauma for the patient. Moreover, a separate trocar and cannula are required to form the incised tract prior to insertion of the measuring device through the tract.

Therefore, there exists a need in the art for a surgical tool for the measurement of an incised tract length which does not require insertion or removal via the esophagus. Moreover, there exists a need in the art for a surgical tool which is capable of creating and measuring an incised tract.

SUMMARY OF THE INVENTION

In accordance with the present invention, a surgical tool is provided to form a tract extending from an external surface of a living body to an internal body cavity, and to measure the length of the tract so formed. The surgical tool includes a handle means having first and second relatively movable handle sections, a cannula attached to the second handle section, and a flexible tubular member covering at least a portion of the cannula and being attached to the first handle section. The flexible tubular member includes an outwardly deformable section which is adapted to be manually movable between undeformed and outwardly deformed configurations.

In further accordance with the present invention, relative movement of the first handle section away from the second handle section causes the deformable section to outwardly deform and thereby define a stop surface. The stop surface is adapted to engage an inner wall of the interior body cavity to prevent removal of the surgical tool from the incised tract. Visible scale indicia provided by the flexible tubular member are visible on an exterior of the body when the stop means engages the inner wall of the interior body cavity to allow the determination of the tract length. The stop surface is located at an origin of the scale indicia.

Preferably, distal ends of the cannula and tubular member are interconnected and covered by a dilator. The dilator includes a central bore through which an obturator extends. The dilator and obturator cooperate to allow the insertion of the surgical tool through the body from the external surface to the internal body cavity. Later removal of the obturator allows the insertion of a guidewire into the internal body cavity to facilitate the placement of a gastrostomy device within the just-formed tract.

Preferably, the first and second handle sections of the handle means are adapted to easily receive a user's fingers, as well as to provide a pair of bearing surfaces. In the preferred embodiment, each of the handle sections includes a forward and a rearward surface against which the user's force is directed to alternatively move the handle sections relatively toward or away from each other.

In further accordance with the invention, a method of forming and measuring a tract with the device of the above-noted type includes the steps of inserting the device from an external body surface into an internal body cavity, outwardly deforming a portion of the tubular member to form a stop surface, engaging the stop surface with an interior wall of the inner body cavity, and viewing the tract length indicating means to determine the tract length.

In further accordance with the present invention, a method of sizing and placing a gastrostomy device within an incised tract comprises the above-mentioned tract formation and measurement steps in addition to the steps of choosing an appropriately sized gastrostomy device in accordance with the measured tract length, positioning the gastrostomy device within the inner body cavity and inserting a portion of the gastrostomy device through the incised tract. Preferably, the gastrostomy device includes an enlarged intragastric portion, a tubular midportion, and an external portion.

BRIEF DESCRIPTION OF THE DRAWINGS

These and further objects of the present invention will be apparent with reference to the following description and drawings, wherein.

DETAILED DESCRIPTION OF THE PREFERRED EMBODIMENTS

Figure 1:
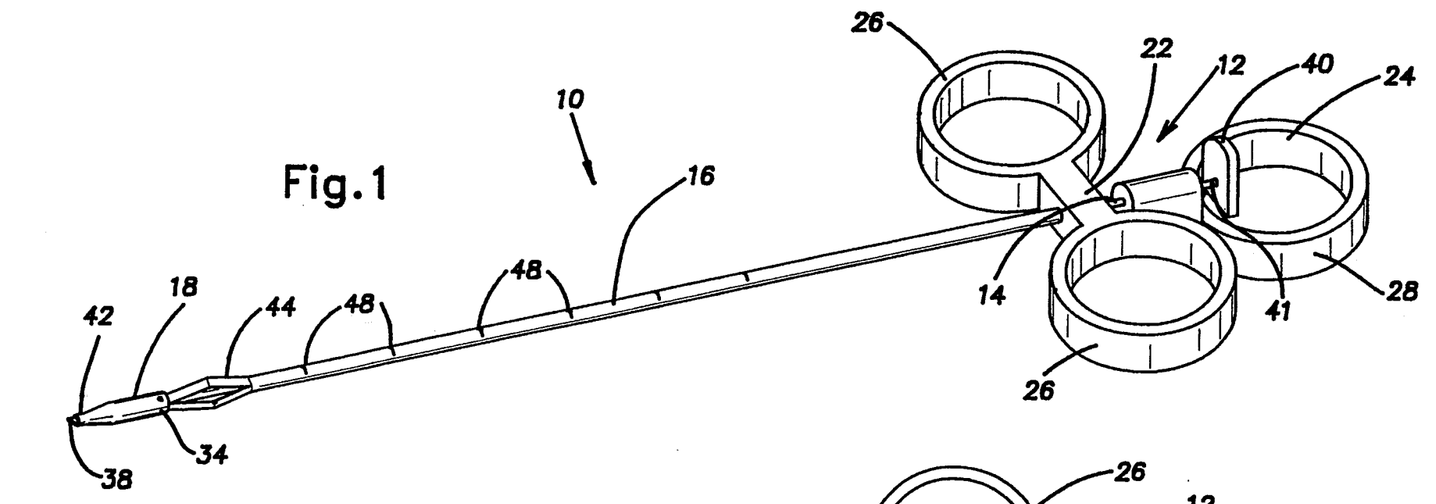
FIG. 1 is a perspective view of a surgical tool in accordance with a first embodiment of the present invention.
Figure 2:
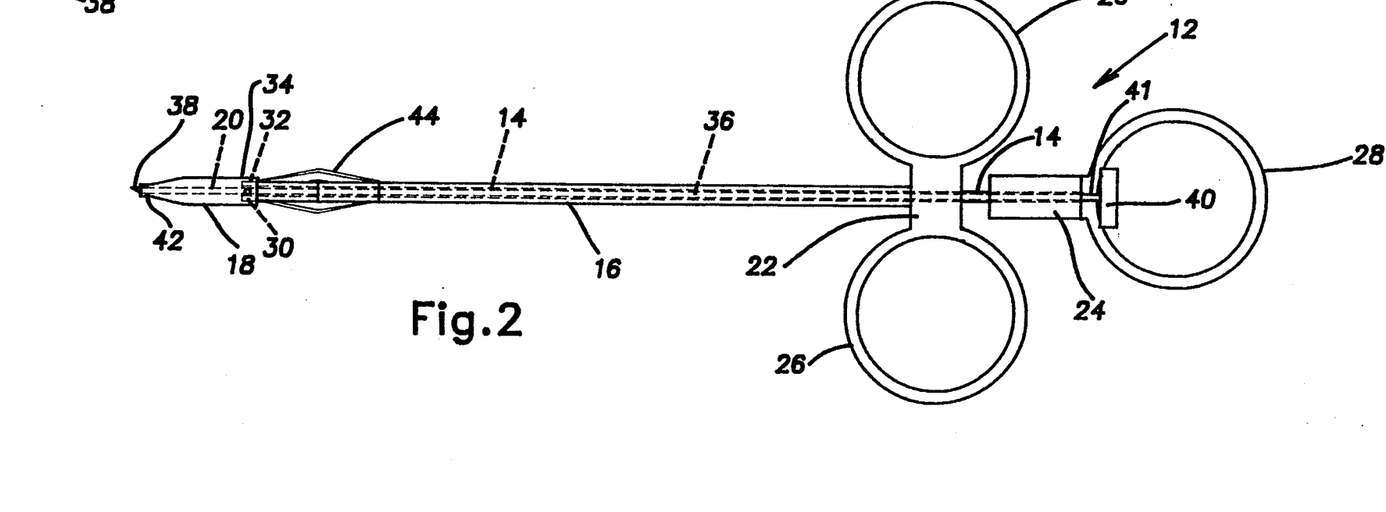
FIG. 2 is a top plan view of the surgical tool in accordance with a first embodiment of the present invention.

With reference to FIGS. 1 and 2, a surgical tool 10 in accordance with a first embodiment is shown. The surgical tool includes a handle means 12, a cannula 14, a flexible outer tubular member 16, a dilator 18, and an obturator 20.

The handle means 12 includes first and second handle sections 22 and 24. As illustrated, the first handle section 22 is bifurcated, having a pair of diametrically opposed ring-shaped finger receiving portions 26. The second handle section 24 includes a single ring-shaped finger receiving portion 28.

Preferably, and as will be recognized by one skilled in the art, the first handle section 22 is adapted to receive a pair of fingers while the second handle section 24 is adapted to receive a single finger and, more specifically, a thumb. The first and second handle sections 22 and 24 are relatively movable towards and away from each other by retaining one of the first or second sections and moving the other section. As will be recognized by one skilled in the art, each of the first and second handle sections 22, 24 include a pair of bearing surfaces to facilitate moving the handle sections relative to each other.

The cannula 14 includes a distal end 30 which is attached to a distal end 32 of the tubular member 16 and a proximal end 34 of the dilator 18. As illustrated, the dilator 18 preferably is crimped, pinned, or otherwise permanently attached to the distal ends of the cannula 14 and tubular member 16.

The cannula 14 is enclosed by the tubular member 16 between the dilator 18 and the first handle section 22. The cannula 14 is slidably received by the first handle section 22 and is attached to and extends through the second handle section 24. A lumen 36 provided by the cannula 14 is accessible via the second handle section.

The obturator 20 is slidably received within the cannula lumen 36, and includes a pointed or otherwise sharpened distal end 38 and a handle 40 attached to its proximal end 41. The pointed distal end 38 of the obturator extends out of a distal end 42 of the dilator 18 when the obturator handle 40 engages the second handle section 24, as illustrated in FIG. 2. The obturator handle 40 is positioned and adapted to be engaged by a user's thumb which extends through the second handle section 24, ensuring that the distal end 38 of the obturator 20 extends out of the dilator 18 when the surgical tool 10 is being used to form an incised tract, as will be discussed more fully hereafter.

The flexible tubular member 16 extends between the first handle section 22 and the dilator 18 and slidably receives the cannula 14. Rearwardly spaced a short distance from the distal end 32, the tubular member 16 includes a deformable section 44. The deformable section 44 is formed in the tubular member 16 by a plurality of short longitudinal cuts therethrough. A series of measurement or scale indicia 48 are provided along a portion of the tubular member. Preferably, the deformable section 44 is located at one end or the origin of the scale indicia 48. Naturally, the tubular member 16 could be transparent and the scale indicia 48 placed on the cannula 14 therein without departing from the scope and spirit of the present invention.

Figures 3, 4, 5, 6:
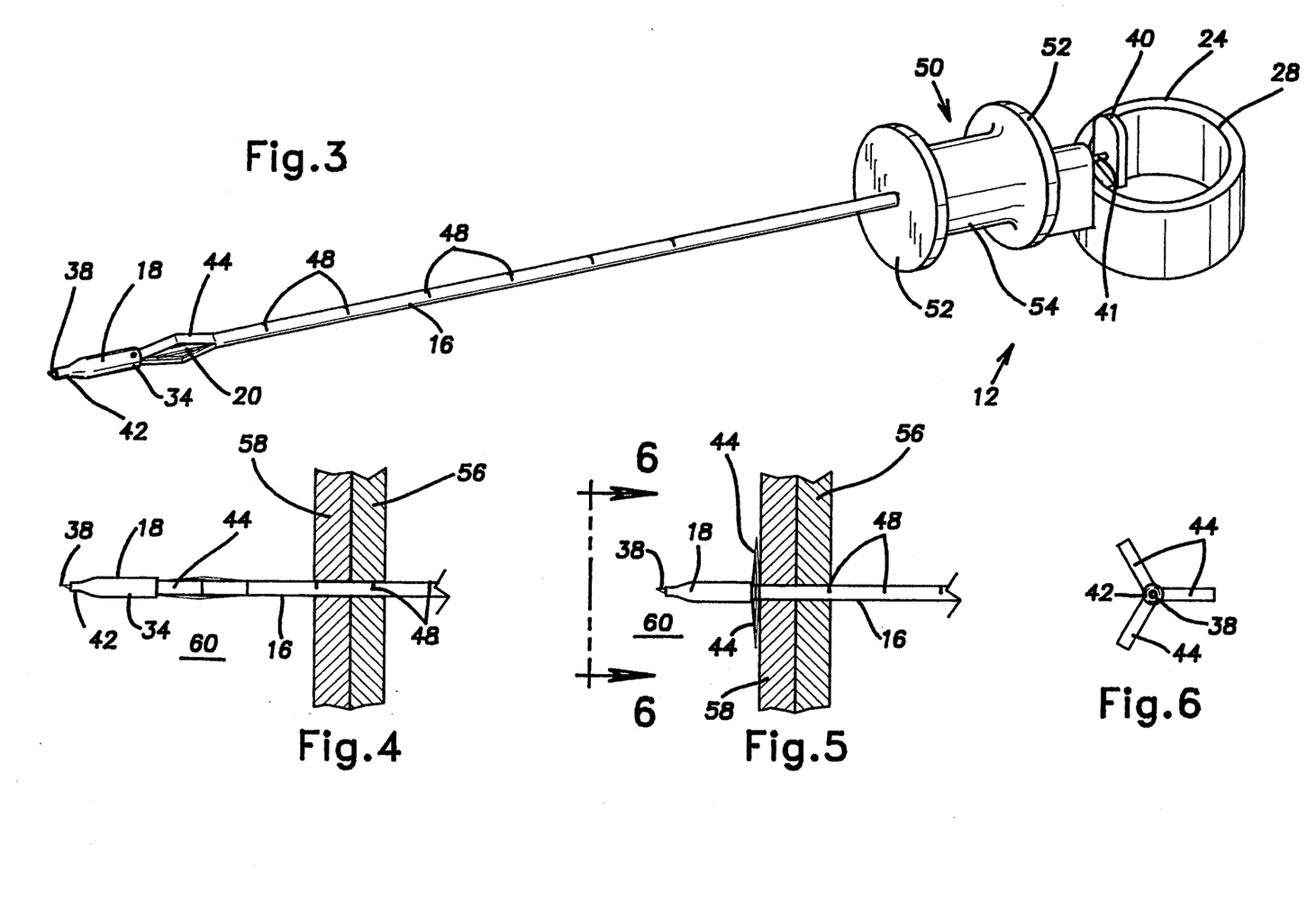
FIG. 3 is a perspective view of a surgical tool in accordance with a further embodiment of the present invention.
FIG. 4 shows an elevational view, partially in cross-section, of the surgical tool extending from an external body surface into an internal body cavity.
FIG. 5 shows an elevational view, partially in cross-section, of the surgical tool with the stop surface engaging an inner wall of an internal body cavity and the scale indicia visible adjacent an exterior surface of the body.
FIG. 6 shows a side elevational view of the terminal end of the surgical tool with the deformable section in the deformed configuration.

As illustrated in FIG. 3, a second embodiment of the present invention is generally identical to the aforementioned first embodiment (FIGS. 1 and 2) with the exception of the first handle section 50. Therefore, identical reference numerals are used when possible. The first handle section 50 of the second embodiment is generally spool-shaped, having proximal and distal annular surfaces 52 which extend radially outward from a generally cylindrical body 54. The remainder of the second embodiment is generally identical to the first embodiment, and will not be described more fully hereinafter.

Use of the surgical tool 10 of either embodiment of the present invention for forming and measuring an incised tract between an external body surface and an internal body cavity, or, more particularly, from the skin to the stomach, is illustrated in FIGS. 4–6. The surgical tool 10, with the sharpened distal end 38 of the obturator 20 projecting out of the distal end 42 of the dilator 18, is inserted through the abdominal wall 56 and stomach wall 58 (FIG. 4) and into the stomach 60. Thereafter, the first and second handle sections 22 and 24 are moved relatively apart, causing the deformable section 44 of the flexible tubular member 16 to outwardly deform (FIG. 6). The surgical tool 10 is pulled relatively away from the body, causing the stop surface defined by the deformed section 44 to engage the stomach wall 58 (FIG. 5). As so positioned, the scale indicia 48 provided by the flexible tubular member 16 are visible adjacent the exterior surface of the body, allowing the length of the incised tract formed by the surgical tool 10 to be measured.

The measurement derived from the scale indicia 48 is used to select a low profile gastrostomy device to be inserted into the incised tract. Preferably, the low profile gastrostomy is of the type described in U.S. Pat. No. 4,863,438, and, most preferably, a gastrostomy device package and method of installation as described in U.S. Pat. No. 5,084,014 is used.

Figure 7:
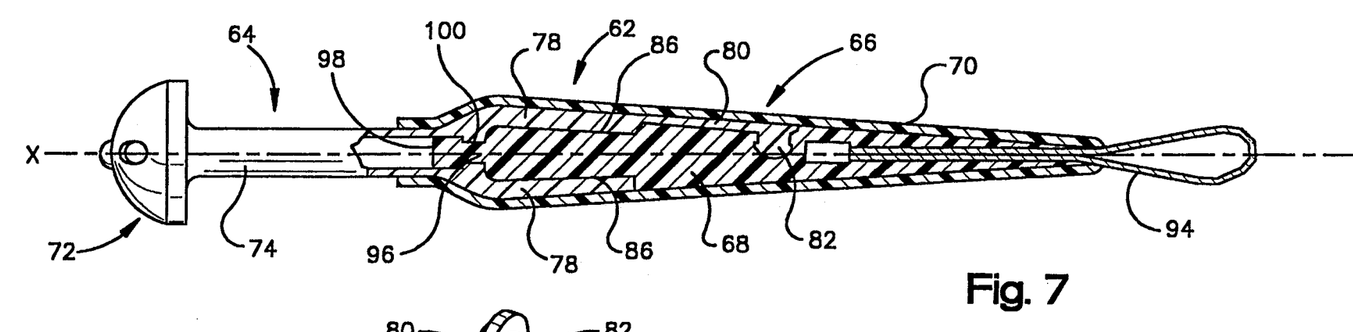
FIG. 7 is a longitudinal, partial, cross-sectional view of a gastrostomy device package to be inserted into the incised tract created and measured in accordance with the present invention.
Figure 8:
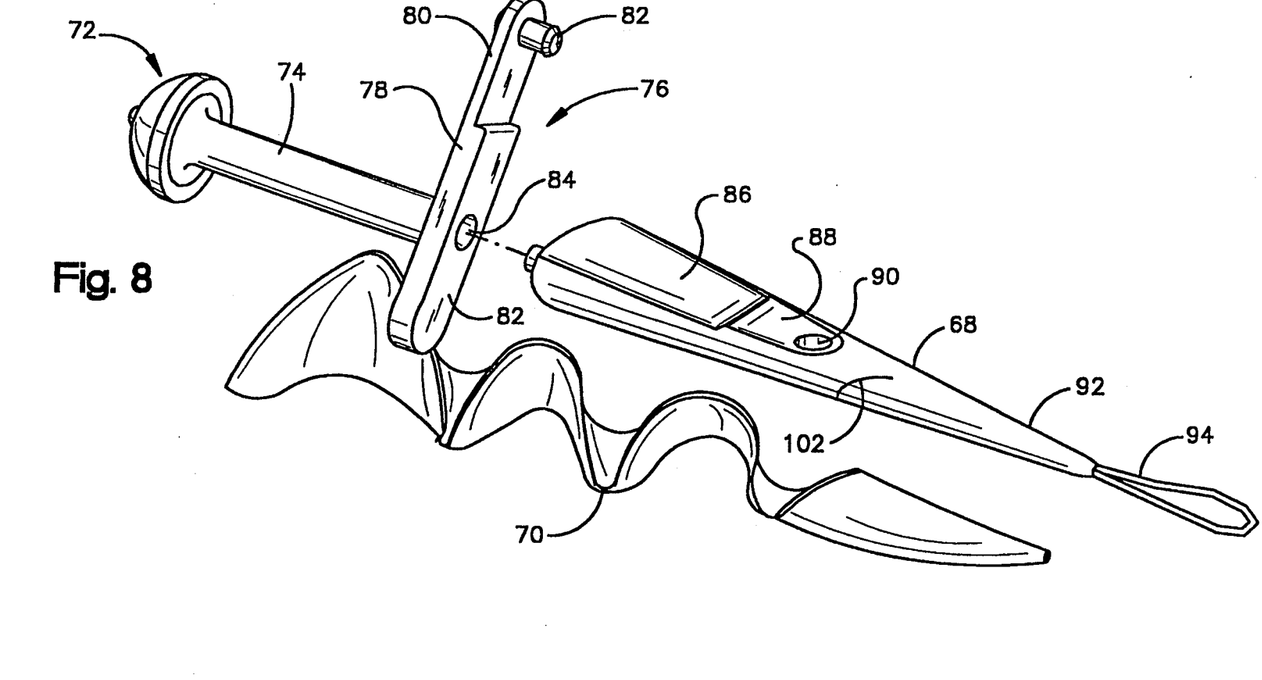
FIG. 8 is an exploded view of the gastrostomy device package of FIG. 7.

Turning to FIGS. 7 and 8, a gastrostomy device package 62 to be inserted into an incised tract which was created and measured in accordance with the present invention is illustrated. The package 62 is generally elongated so as to extend along a longitudinal x—x axis, as illustrated. The package is comprised of two major portions, namely, a low profile gastrostomy device 64, often referred to in the art as a "gastrostomy button", and a shroud means 66 comprised primarily of a dilator member 68, and a plastic film material 70 constituting a tubular sleeve extending generally completely over the dilator 68.

The gastrostomy device 64 includes an intragastric portion 72 located at one end of a tubular midportion 74 having at its other end a resilient external portion 76. The device is preferably formed of a biocompatable silicone rubber material so as to be flexible and elastomeric. The length of the tubular portion 74 is sized to be dimensionally compatible with the combined thickness of, for example, a patient's stomach 58 and abdominal walls 56, which was determined by using the surgical tool 10, as previously described.

The external portion 76 of the gastrostomy device 64 includes a pair of diametrically opposed wing-like projections 78, one of which has extending from it a plug retainer 80 which has a distal end providing a plug 82, wherein the plug retainer 80 can be folded over to permit insertion of the plug 82 into a feeding tube receptor port 84. As is known in the art, when positioned within, for example, a human or animal patient undergoing medical treatment, an enteral feeding tube can be inserted into the port 84 through the tubular midportion 74 and into the intragastric portion 72 to effect the flow of fluid either into or out of a body cavity, such as the patient's stomach, within which the intragastric portion is located. It is to be noted that the intragastric portion 72 includes within the usual normally closed reflux valve (not shown) which prevents egress of fluid outwardly through the tubular midportion 74 when the enteral feeding tube is not maintaining the valve in an open position.

With particular reference to FIG. 7, the flexible wing-like projections 78, including the associated plug retainer 80 and plug 82, are shown in a folded or collapsed condition so that they extend along parallel lines adjacent to the axis x—x, as illustrated- The dilator member 68 which provides a pair of opposed flats or recesses 86 against which the wing-like projections 78 are held in their folded or collapsed position by the plastic film 70 in the preferred form of a tubular sleeve of heat-shrink or shrink-wrap type plastic film. In its collapsed condition, the external portion 76 (FIG. 8) is contained within and compressed by the shroud means 66, and, more specifically, the plastic film 70.

The dilator member 68 further includes a plug retainer recess or flat 88 having a plug recess 90 into which the plug 82 fits, as illustrated in FIG. 7. The dilator member 68 has a tapered distal end 92 which is provided with a pull wire loop 94 embedded within the dilator member, as illustrated. The dilator member is also provided with a reduced diameter portion 96 which forms an inboard part of a retainer tip 98 that extends and snaps into the external end 28, i.e., port 28, of the tubular midportion 74, as illustrated.

The gastrostomy device 64 is provided with an annular or circular lip 100 that fits into the reduced diameter portion 96, constituting a circular groove, so as to provide a releasable locking means holding the gastrostomy device 64 in position relative to the dilator member 68. It can also be seen that an open, or leftward end as viewed in FIG. 7, of the plastic film 70 constituting a tubular sleeve extends beyond and over the circular lip and its associated annular groove constituted by reduced diameter portion 96 of the retainer tip 98, so as to hold and compress the circular lip 100 into the reduced diameter portion 96 of the dilator member 68.

With reference to FIG. 8, a guide groove 102 is provided, as illustrated, on a surface of the dilator member 68 spaced from the external portion 76 of the gastrostomy device 64 when in its position as illustrated in FIG. 7. The guide groove 102 provides an indicator point for a partially cutting the plastic film 70 and peeling it around and away from the dilator member 68, as illustrated in FIG. 8, so that the gastrostomy device 64 and the dilator member 68 can be separated from each other so as to allow the resilient wing-like projections 78 to return to a normal expanded position as illustrated in FIG. 8.

Thus, FIG. 7 illustrates a gastrostomy device package 62 for initial placement of the gastrostomy device 64 in a patient, as discussed below, while FIG. 8 illustrates the package 62 in a disassembled form after the device 64 has been placed within an incision in the patient, as will now be discussed.

Figures 9A, 9B, 9C, 9D, 9E, 9F, 9G:
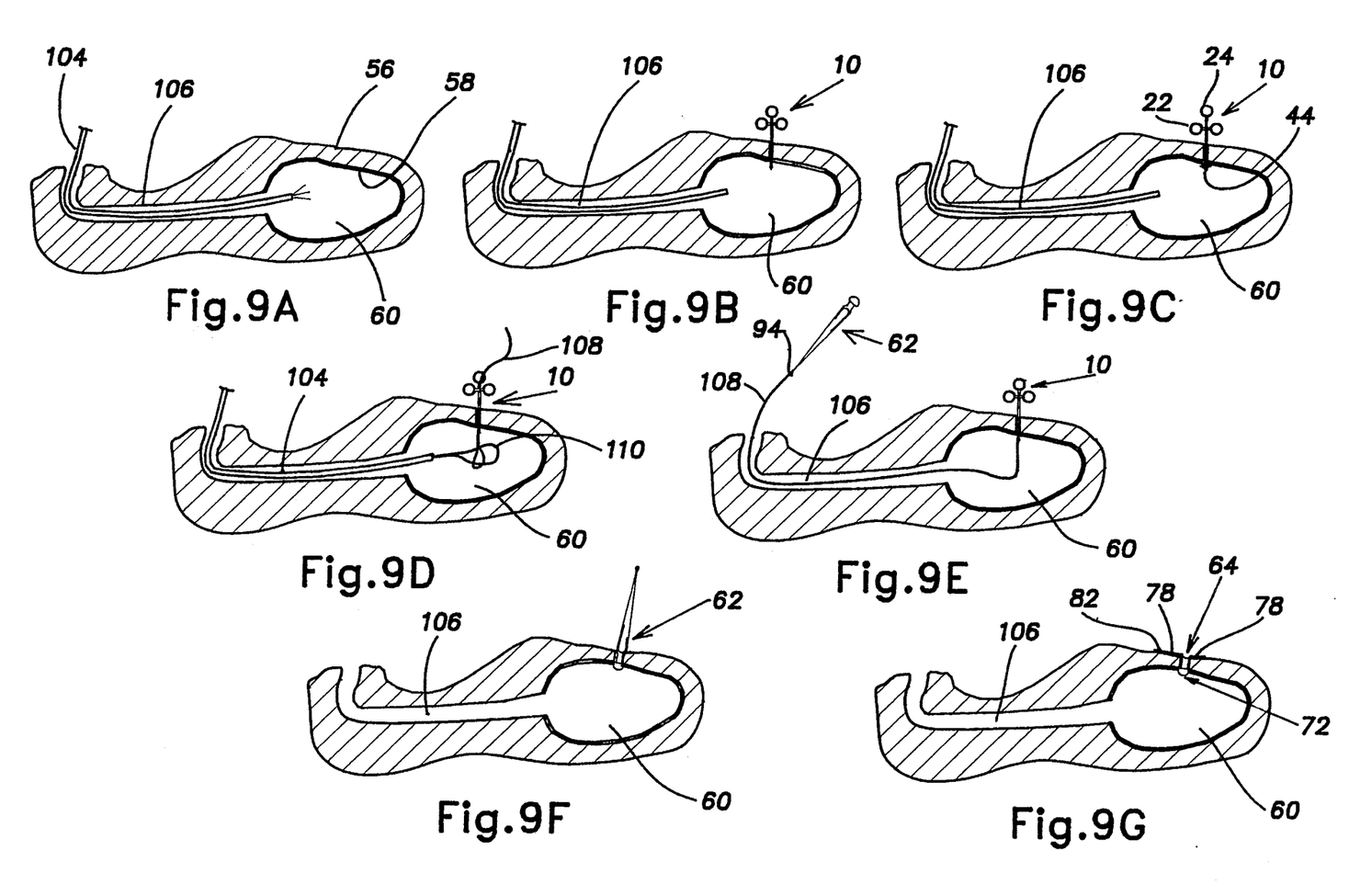
FIGS. 9A–9G sequentially illustrate the methodology for creating and measuring an incised tract, as well as for placing a gastrostomy device within the incised tract.

Turning to FIG. 9A, there is schematically illustrated a patient having an inner body cavity such as a stomach 60 within which is to be placed the gastrostomy device 64 in accordance with the present invention. It is to be noted that the gastrostomy device package 62 and method of placement described hereinafter are more fully described in incorporated U.S. Pat. No. 5,084,014. Moreover, the surgical tool 10 and method of use can be used for creating and measuring incised tracts into other viscera of the body for other applications, such as, for example, urinary bladder drainage, ileostomy, jejunostomy, and cystostomy.

The outer surface or skin of the patient extends over the abdominal wall 56, which in turn abuts the stomach wall 58. In a first step for placing the gastrostomy device package 62, the stomach 60 of the patient is insufflated via an endoscope tube 104 extending down through the esophagus 106 of the patient, as illustrated. As illustrated in FIG. 9B, the surgical tool 10 of the present invention is inserted through the abdominal and stomach walls 56 and 58 of the patient to establish an incised tract that will receive a gastrostomy button (FIG. 4).

As shown in FIG. 9C, the first and second handle sections 22 and 24 are moved generally away from each other, deforming the deformable section 44 of the flexible tubular member 16 to define a stop surface. Thereafter, the surgical tool 10 is pulled outwardly, placing the stop surface in engagement with the inner surface of the stomach wall 58 and allowing the length of the incised tract to be determined via the scale indicia 48 on the tubular member 16 which is visible adjacent the external body surface (FIG. 5).

As shown in FIG. 9D, with the obturator 20 removed from the cannula 14, a pull wire 108 is inserted through the cannula lumen so that its end can be captured by a snare 110 extending through the endoscope tube 104. With further reference to FIG. 9E, the pull wire 108 has been pulled outwardly through the patient's mouth so that the pull wire loop 94 of the gastrostomy device package 62 can be attached, as illustrated.

Turning to FIG. 9F, the gastrostomy device package 62, by use of the pull wire 108, has been pulled down the esophagus 106 of the patient, and then through the incision provided by the surgical tool 10. Generally, the gastrostomy device package 62 is the same or larger in diameter as the tubular member 16 of the surgical tool so that the package pushes the surgical tool 10 out of the incised tract as it is inserted therein.

Turning to FIG. 9G, the intragastric portion 72 of the gastrostomy device 64 is now located within the stomach 60 of the patient, while a tubular midportion 74 extends through the stomach wall 58 and abdominal wall 56, with the wing-like projections 78 in the extended, uncollapsed, normal position engaging the outer surface of the abdominal wall 56, wherein the gastrostomy device 64 is now retained in position.

By use of the surgical tool 10 to create and measure the incised tract, and the gastrostomy device package 62 and methodology for placing it as illustrated in FIGS. 9A–9G, the use of the traditional enteral feeding tube to establish a fistulas stoma tract is avoided. Thus the cost and patient trauma associated therewith are eliminated, and the inherent benefits afforded by the low profile gastrostomy device are available at an earlier point in time to the patient requiring a gastrostomy.

While the preferred embodiments of the present invention are shown and described herein, it is to be understood that the same is not so limited but shall cover and include any and all modifications thereof which fall within the purview of the invention.

What is claimed is:

1. A surgical tool for forming an incised tract and for measuring the tract so formed, comprising a handle means having first and second relatively movable handle sections, at least one of said first and second handle sections having a ring-shaped finger receiving portion,- .said finger receiving portion providing bearing surfaces to facilitate movement of said first and second handle sections toward and away from one another, a cannula slidably movable with respect to the first handle section, an obturator slidably received by the cannula, a dilator secured to one end of the cannula and the second handle section being secured to an opposite end of the cannula, said dilator having a sharpened distal end of the obturator projecting out of a distal end thereof, said sharpened end of the obturator and said dilator cooperating to form the incised tract when forced into and through a body being operated upon, and a flexible tubular member generally covering at least a portion of the cannula and including an outwardly deformable section, said tubular member having a proximal end secured to the first handle section and a distal end secured to the dilator, wherein movement of the first handle section relative to the second handle section causes the deformable section of the tubular member to outwardly deform and thereby define a stop surface, said stop surface being adapted to engage a surface surrounding an inner terminal end of the tract being measured, wherein a portion of the tubular member projecting from an outer terminal end of the tract includes scale indicia which are used to determine the tract length.

2. A surgical tool as recited in claim 1, wherein the cannula is slidably received by the first handle section.

3. A surgical tool as recited in claim 1, wherein the deformable section is formed by longitudinally cutting the tubular member.

4. A surgical tool as recited in claim 3, wherein the deformable section is adjacent the dilator.

5. A surgical tool for forming and measuring an incised tract in a body, comprising a handle means having first and second relatively movable handle sections, at least one Of said first and second handle sections having a ring-shaped finger receiving portion, said finger receiving portion providing bearing surfaces to facilitate movement of said first and second handle sections toward and away from one another, a cannula secured to the second handle section, an obturator slidably and removably insertable within a lumen provided by the cannula, said obturator having a sharpened distal end which is adapted to form the incised tract, and a tubular member covering at least a portion of the cannula and having a proximal end secured to the first handle section and a distal end secured to the cannula, wherein longitudinal movement of the first handle section and cannula relative to the second handle section causes a deformable section provided by the tubular member to outwardly deform and thereby define a stop surface, said stop surface being engageable with a wall surrounding an inner terminal end of the tract, and tract length indicating means, said tract length indicating means being provided by one of the cannula or tubular member and being visible adjacent an external surface of the body when the stop surface engages the inner wall, said tract length indicating means being adapted to allow the tract length to be measured.

6. A surgical tool as recited in claim 5, wherein distal ends of the cannula and tubular member are secured to a dilator.

7. A surgical tool as in claim 6, wherein the sharpened distal end of the obturator slidably projects from an end of the dilator.

8. A surgical tool as in claim 7, wherein the deformable section is adjacent the dilator.

9. A surgical tool as in claim 8, wherein the tract length indicating means comprise scale indicia on the tubular member.

10. A surgical tool as in claim 5, wherein the tract length indicating means comprise scale indicia on the tubular member.

11. A tract measuring device, comprising a handle means comprising first and second relatively movable handle sections, a cannula secured to the second handle section, an obturator slidably received within the cannula and having a sharpened distal end projecting out of the cannula, a tubular member generally covering at least a portion of the cannula and including an outwardly deformable section, said tubular member having a proximal end attached to the first handle section and a distal end attached to the cannula, at least one of said first and second handle sections have a ring-shaped finger receiving portion, said finger receiving portion providing bearing surfaces to facilitate movement of said first and second handle sections toward and away from one another, wherein relative movement of the first handle section away from the second handle section causes the deformable section of the tubular member to outwardly deform and thereby define a stop surface, said stop surface being adapted to engage an internal wall surrounding an inner end of the tract being measured, and tract length indicating means, said indicating means being provided by either the cannula or the tubular member and being visible adjacent an external surface of the body when the stop surface engages the internal wall.

12. A device as recited in claim 11, wherein the tract length indicating means comprises scale indicia, said scale indicia being located on the tubular member.

13. A device as recited in claim 12, wherein the cannula is slidably received by the first handle section.

14. A device as recited in claim 13, wherein lumen of the cannula is accessible at the second handle section.

15. A surgical tool for the formation and measurement of an incised tract in a body, said tract extending from an exterior surface of the body to an internal body cavity, comprising:

first and second handle members, at least one of said first and second handle members having a ring-shaped finger receiving portion, said finger receiving portion providing bearing surfaces to facilitate movement of said first and second handle members toward and away from one another;

means for forming an incised tract, said tract forming means including an obturator and a dilator, said obturator having a sharpened distal end which projects from the dilator and is operable to pierce tissue and thereby form the incised tract as the surgical tool is inserted into the body, said dilator being operable to enlarge the tract during insertion of the surgical tool into the body;

a deformable member on said tract forming means, said deformable member defining a stop surface which is adapted to engage an inner wall defining said cavity;

means for deforming said deformable member by movement of said handle members;

means for measuring the incised tract length, said measuring means located on said tract forming means and being visible adjacent the exterior surface of the body to indicate tract length.

16. A surgical tool as recited in claim 15, wherein the tract forming means further comprises a cannula, the obturator being slidably received within said cannula, said dilator being secured to the cannula.

17. A surgical tool as recited in claim 16, wherein a tubular member comprises the deformable member and encloses a portion of the cannula.

18. (amended) A surgical tool as recited in claim 17, wherein the deforming means comprise the handle members, the cannula and the tubular member, the tubular member is secured at opposite ends to one of the handle members and a distal end of the cannula while a proximal end of the cannula is secured to the other of the handle members such that movement of the handle members relatively away from each other causes the cannula to slide within the tubular member, compressing the tubular member and outwardly deforming the deformable member.

19. A surgical tool as recited in claim 18, wherein the deformable member is adjacent the dilator.

20. A surgical tool as recited in claim 19, wherein the tract length indicating means comprise scale indicia on the tubular member.

* * * * *

UNITED STATES PATENT AND TRADEMARK OFFICE
CERTIFICATE OF CORRECTION

PATENT NO. : 5,356,382

DATED : October 18, 1994

INVENTOR(S) : Picha et al.

It is certified that error appears in the above-identified patent and that said Letters Patent is hereby corrected as shown below:

Column 7, line 55, delete "illustrated-" and insert --illustrated.--.

Column 9, lines 44 and 45, (Claim 1, lines 5 and 6), delete "portion,-.said" and insert --portion, said--.

Column 10, line 13, (Claim 5, line 4) delete "Of" and insert --of--.

Column 12, line 18, (Claim 18, line 1) delete "(amended)".

Signed and Sealed this

Third Day of January, 1995

Attest:

BRUCE LEHMAN

Attesting Officer     Commissioner of Patents and Trademarks